(12) United States Patent
Almond et al.

(10) Patent No.: US 11,267,643 B2
(45) Date of Patent: Mar. 8, 2022

(54) CONTACT LENS DISPENSER

(71) Applicant: CooperVision International Limited, Fareham (GB)

(72) Inventors: Sarah Almond, Southampton (GB); Carlos Ortiz, Pittsford, NY (US); Gary Hunt, Bristol (GB); Mike Nelson, Bristol (GB); Russell Beard, Bristol (GB); Thomas Harkin, Bristol (GB); Pauline Gavelle, Toulouse (FR)

(73) Assignee: COOPERVISION INTERNATIONAL LIMITED, Fareham (GB)

( * ) Notice: Subject to any disclaimer, the term of this patent is extended or adjusted under 35 U.S.C. 154(b) by 78 days.

(21) Appl. No.: 16/737,940

(22) Filed: Jan. 9, 2020

(65) Prior Publication Data

US 2020/0231367 A1    Jul. 23, 2020

Related U.S. Application Data

(60) Provisional application No. 62/795,305, filed on Jan. 22, 2019.

(51) Int. Cl.
*B65D 83/00* (2006.01)
*A45C 11/00* (2006.01)

(52) U.S. Cl.
CPC ........ *B65D 83/0083* (2013.01); *A45C 11/005* (2013.01)

(58) Field of Classification Search
CPC ... A45C 11/04; A45C 11/005; B65D 83/0083; B65D 83/0027; B65D 83/0005;
(Continued)

(56) References Cited

U.S. PATENT DOCUMENTS

| 213,555 A | * | 3/1879 | Evans | F41A 9/72 |
| | | | | 42/49.01 |
| 1,451,775 A | * | 4/1923 | Husch | A46B 9/045 |
| | | | | 15/194 |

(Continued)

FOREIGN PATENT DOCUMENTS

| AU | 739045 B2 | 10/2001 |
| EP | 0734958 A1 | 10/1996 |

(Continued)

OTHER PUBLICATIONS

International Search Report and Written Opinion issued in corresponding International Patent Application No. PCT/GB2020/050113 dated Jul. 13, 2020 (24 pages).

(Continued)

*Primary Examiner* — Rakesh Kumar
(74) *Attorney, Agent, or Firm* — Kilyk & Bowersox, P.L.L.C.

(57) ABSTRACT

Contact lens dispensers are provided including a pens dispenser having an interior and a dispensing end. A delivery screw is provided in the interior of the tubular housing. The delivery screw has a thread pitch and a plurality of contact lenses, one contact lens per pitch. Upon actuation of an actuator, each contact lens moves along the thread by a distance of one pitch and a single contact lens is dispensed from the dispensing end of the tubular housing. A case and disposable foil contact lens cartridge are also provided as a re a case and disposable contact lens foil spool, wherein actuation of push-buttons dispense contact lenses ready for immediate application onto an eye.

7 Claims, 5 Drawing Sheets

(58) Field of Classification Search
CPC ........... B65D 83/0011; B65D 83/0409; B65D 83/04; B65D 25/00; B65D 25/52; B65D 83/005; B65D 25/525; B65D 83/0454
USPC ........... 206/5.1, 499; 53/475; 221/211, 296, 221/210, 198, 226, 231, 277
See application file for complete search history.

(56) References Cited

U.S. PATENT DOCUMENTS

| | | | | |
|---|---|---|---|---|
| 2,711,226 | A * | 6/1955 | Davis, Jr. | B03C 3/15 96/61 |
| 2,813,289 | A * | 11/1957 | Even | A45D 29/007 401/202 |
| 3,162,322 | A * | 12/1964 | Gilbertson | B65D 83/02 221/135 |
| 3,706,394 | A * | 12/1972 | Merz | A47F 1/06 221/75 |
| 3,715,055 | A * | 2/1973 | Kendrick et al. | B65G 53/30 221/75 |
| 4,173,281 | A * | 11/1979 | Trought | A61F 2/1691 206/210 |
| 4,691,820 | A | 9/1987 | Martinez | |
| D299,085 | S | 12/1988 | Martinez | |
| D305,478 | S | 1/1990 | Lahm et al. | |
| 4,965,951 | A * | 10/1990 | Miller | F41A 9/77 42/49.01 |
| 5,069,494 | A | 12/1991 | Reinson et al. | |
| 5,341,954 | A * | 8/1994 | Smith | G07F 11/42 221/85 |
| 5,409,104 | A | 4/1995 | Lovell | |
| 5,520,171 | A * | 5/1996 | David | F41A 9/77 124/51.1 |
| 5,609,246 | A | 3/1997 | Borghorst et al. | |
| 5,620,088 | A | 4/1997 | Martin et al. | |
| 5,685,420 | A | 11/1997 | Martin et al. | |
| 5,697,495 | A | 12/1997 | Abrams et al. | |
| 5,704,468 | A | 1/1998 | Lust et al. | |
| 6,004,054 | A * | 12/1999 | Wei-Pin | A45D 40/06 401/78 |
| 6,044,966 | A | 4/2000 | Haase | |
| 6,260,695 | B1 * | 7/2001 | Tasber | B65B 25/008 206/499 |
| 6,398,018 | B1 | 6/2002 | Livesley et al. | |
| 6,471,052 | B2 | 10/2002 | Faxe et al. | |
| 6,474,465 | B1 | 11/2002 | Jux | |
| 6,572,165 | B2 | 6/2003 | Faxe et al. | |
| 6,889,825 | B2 | 5/2005 | Ichikawa et al. | |
| 6,978,776 | B2 * | 12/2005 | Hamilton | F41A 9/77 124/51.1 |
| 6,997,344 | B2 | 2/2006 | Brown et al. | |
| 7,086,526 | B2 | 8/2006 | Newman | |
| 7,168,746 | B2 | 1/2007 | Py | |
| 7,367,471 | B1 * | 5/2008 | Ip | G07F 11/36 221/75 |
| 7,426,993 | B2 | 9/2008 | Coldrey et al. | |
| 7,431,152 | B2 | 10/2008 | Marmo | |
| 7,455,166 | B2 * | 11/2008 | Seiffert | B65B 5/103 193/44 |
| 7,477,366 | B2 | 1/2009 | Clements et al. | |
| 7,640,894 | B2 * | 1/2010 | Jager | A01K 15/026 119/710 |
| 7,699,161 | B2 | 4/2010 | Fokarski et al. | |
| 7,770,732 | B2 | 8/2010 | Stroppolo et al. | |
| 7,784,608 | B2 | 8/2010 | Tokarski et al. | |
| 7,789,266 | B2 | 9/2010 | Biel et al. | |
| 7,816,455 | B2 | 10/2010 | Marmo | |
| 7,892,473 | B2 * | 2/2011 | Aylward | B65B 35/12 264/401 |
| 7,921,834 | B2 * | 4/2011 | Hamilton | F41B 11/53 124/51.1 |
| 8,061,897 | B2 | 11/2011 | Ichikawa et al. | |
| 8,069,979 | B2 | 12/2011 | Newman et al. | |
| 8,281,920 | B2 | 10/2012 | Tokarski et al. | |
| 8,317,016 | B2 | 11/2012 | Tokarski et al. | |
| 8,459,445 | B2 | 6/2013 | Newman | |
| 8,833,548 | B2 | 9/2014 | Hsieh et al. | |
| 8,955,672 | B2 | 2/2015 | Newman | |
| 9,095,670 | B2 | 8/2015 | Briant et al. | |
| 9,102,457 | B2 * | 8/2015 | Parrish | B65G 59/00 |
| 9,119,450 | B2 | 9/2015 | Lee et al. | |
| 9,173,463 | B2 | 11/2015 | Clamp et al. | |
| 9,439,487 | B2 | 9/2016 | Barre et al. | |
| 9,499,286 | B2 * | 11/2016 | Parrish | B65G 59/00 |
| 9,655,423 | B1 | 5/2017 | Wang | |
| 9,701,458 | B2 | 7/2017 | Barrows et al. | |
| 9,764,888 | B2 * | 9/2017 | Tiesberger | B65D 83/0409 |
| 9,839,270 | B2 | 12/2017 | Howell et al. | |
| D813,537 | S | 3/2018 | Miura et al. | |
| 10,092,075 | B2 | 10/2018 | Barre et al. | |
| 2006/0054514 | A1 | 3/2006 | Tokarski et al. | |
| 2006/0151521 | A1 * | 7/2006 | Toker | B65D 83/0409 221/226 |
| 2006/0260957 | A1 | 11/2006 | Hamilton | |
| 2007/0000792 | A1 * | 1/2007 | Newman | B65D 83/0418 206/5.1 |
| 2007/0119720 | A1 | 5/2007 | Marmo | |
| 2007/0289553 | A1 * | 12/2007 | Jager | A01K 15/026 119/710 |
| 2008/0132438 | A1 * | 6/2008 | Hoffman | A01N 31/02 510/380 |
| 2009/0139879 | A1 | 6/2009 | Tokarski et al. | |
| 2010/0300902 | A1 | 12/2010 | Marmo | |
| 2012/0055817 | A1 | 3/2012 | Newman et al. | |
| 2012/0267262 | A1 | 10/2012 | Wang et al. | |
| 2014/0246337 | A1 | 9/2014 | Newman | |
| 2014/0262845 | A1 | 9/2014 | Newman | |
| 2015/0114851 | A1 | 4/2015 | English et al. | |
| 2017/0086552 | A1 | 3/2017 | Michalos | |
| 2017/0096272 | A1 | 4/2017 | Coon et al. | |
| 2017/0165901 | A1 | 6/2017 | Fischer et al. | |
| 2018/0125189 | A1 | 5/2018 | Barre et al. | |
| 2019/0008251 | A1 | 1/2019 | Kim | |
| 2020/0231367 | A1 * | 7/2020 | Almond | B65D 83/0409 |

FOREIGN PATENT DOCUMENTS

| | | | |
|---|---|---|---|
| JP | 2008253746 A | 10/2008 | |
| JP | 5466344 B1 | 4/2014 | |
| JP | 5676760 B2 | 2/2015 | |
| JP | 2016221059 A | 12/2016 | |
| LU | 88593 A1 | 9/1995 | |
| TW | 201302567 A1 | 1/2013 | |
| WO | 0043287 A1 | 7/2000 | |
| WO | WO-0076881 A1 * | 12/2000 | B65D 85/00 |
| WO | 2009102273 A1 | 8/2009 | |
| WO | 2011112998 A2 | 9/2011 | |
| WO | 2012131786 A1 | 10/2012 | |
| WO | 2012168964 A1 | 12/2012 | |
| WO | 2013136361 A1 | 9/2013 | |
| WO | 2013153582 A1 | 10/2013 | |
| WO | 2014195588 A1 | 12/2014 | |
| WO | 2017137738 A1 | 8/2017 | |

OTHER PUBLICATIONS

International Preliminary Report on Patentability issued in corresponding International Patent Application No. PCT/GB2020/050113 dated Apr. 30, 2021 (22 pages).

International Search Report and Written Opinion issued in corresponding International Patent Application No. PCT/GB2020/050113 dated Jul. 16, 2020 (23 pages).

* cited by examiner

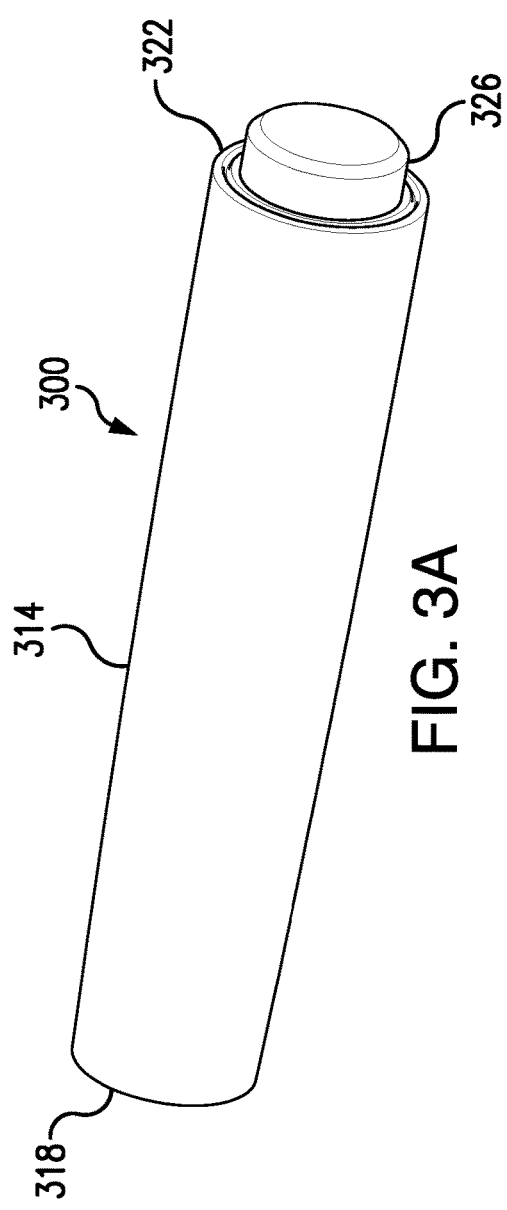
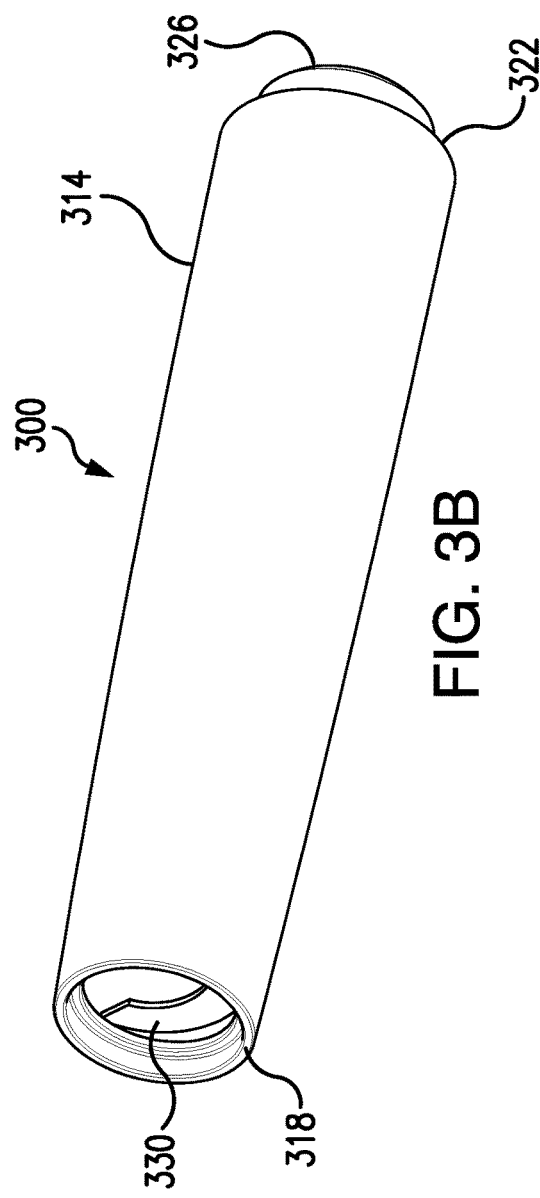

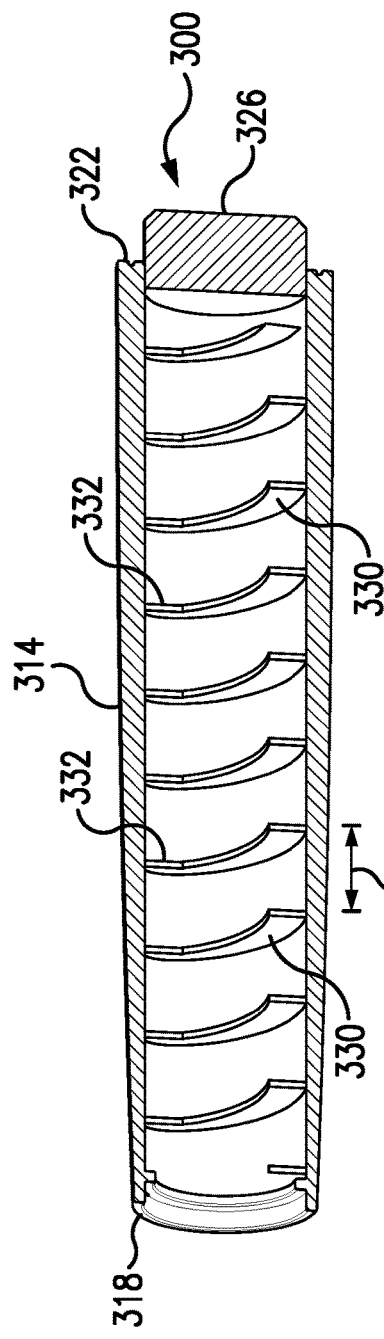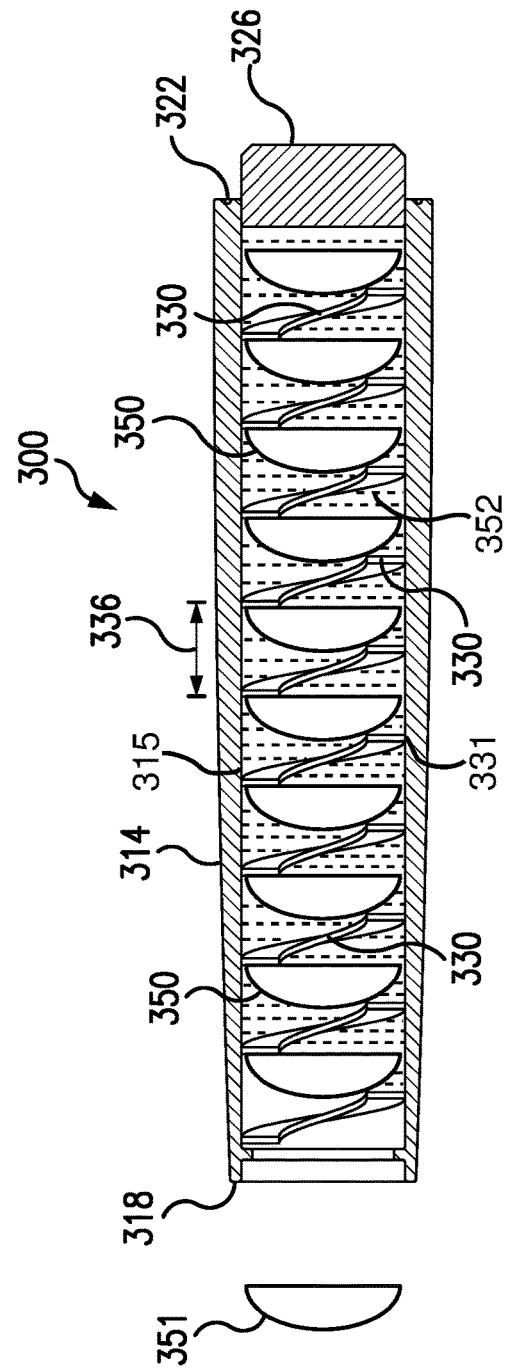

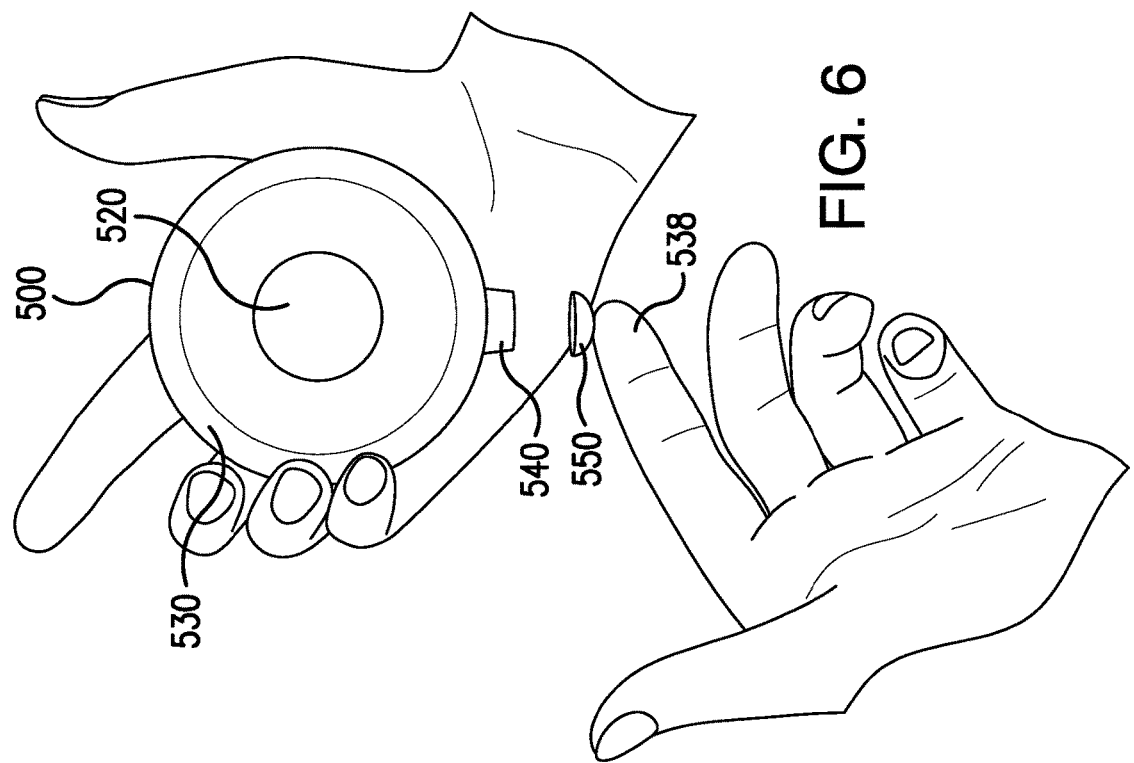
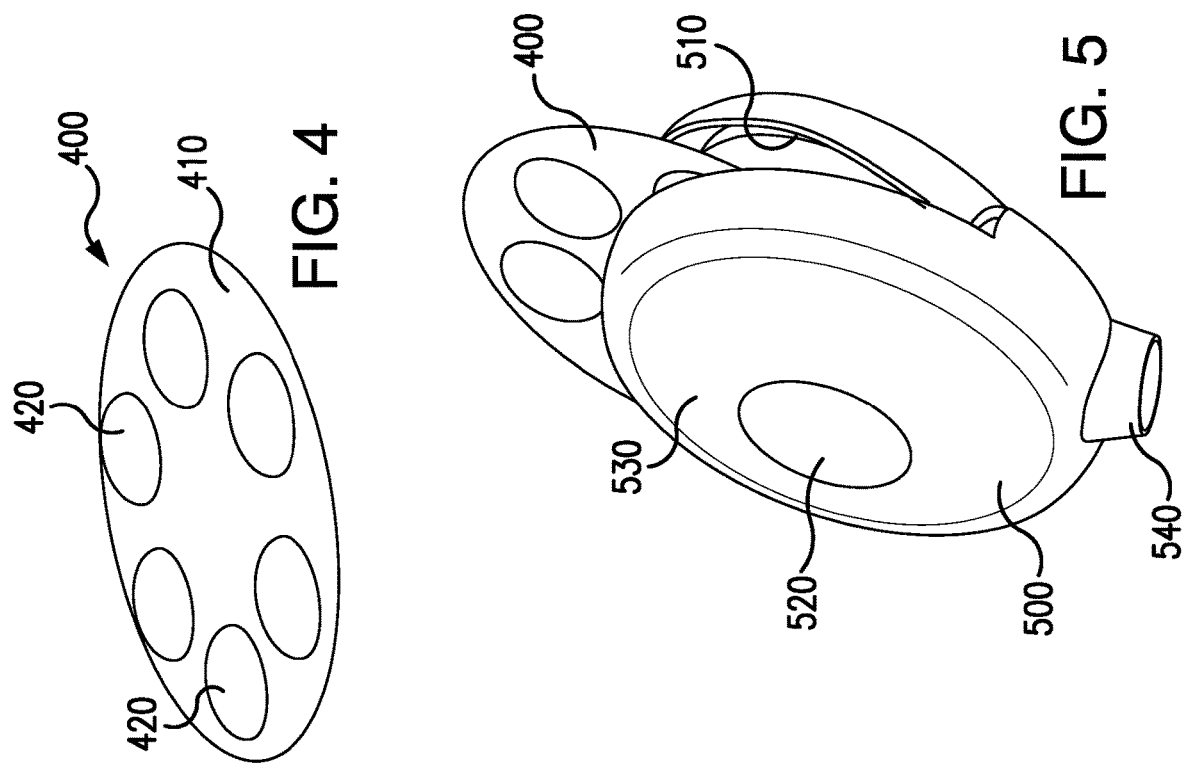

CONTACT LENS DISPENSER

This application claims the benefit under 35 U.S.C. § 119(e) of prior U.S. Provisional Patent Application No. 62/795,305, filed Jan. 22, 2019, which is incorporated in its entirety by reference herein.

FIELD OF THE INVENTION

The present invention relates to contact lens packaging and methods, and more specifically, to blister packages for sealed contact lenses containing unworn contact lenses, and methods of manufacturing packaged contact lenses.

BACKGROUND TO THE INVENTION

Contact lenses, such as hydrogel and silicone hydrogel contact lenses, are frequently packaged in sealed blister packages or blister packs that permit storage of the unworn contact lenses in a sterile environment. For instance, a blister package which is adapted to provide a sterile sealed storage environment for a disposable or single-use hydrophilic contact lens, wherein the lens is immersed in a sterile aqueous solution, for example, such as in an isotonic saline solution, is described in Martinez, U.S. Pat. No. 4,691,820. Additional contact lens packages are disclosed in U.S. Pat. Nos. 4,691,820; 5,054,610; 5,337,888; 5,375,698; 5,409,104; 5,467,868; 5,515,964; 5,609,246; 5,620,088; 5,695,049; 5,697,495; 5,704,468; 5,711,416; 5,722,536; 5,573,108; 5,823,327; 5,704,468; 5,983,608; 6,029,808; 6,044,966; and 6,401,915.

As an example of part of a manufacturing process, a newly manufactured unworn contact lens will be placed in a cavity or bowl of a plastic base member of a contact lens blister package, a contact lens packaging solution will be provided in the blister package cavity, and a foil sealing member will be adhered to the blister package to hermetically seal the contact lens in the packaging solution in the cavity. In other words, a contact lens blister package used in the manufacture of contact lenses contains a base member having a cavity or bowl, an unworn contact lens provided in a packaging solution within the cavity, and a sealing member sealed to the base member to provide an air tight seal around the perimeter of the cavity. The sealed blister package containing the contact lens is then autoclaved to sterilize the contact lens in the packaging solution in the cavity. The blister packs are understood to be primary packaging. Multiple blister packs are then placed in cartons. The cartons are considered secondary packaging.

Contact lens packages typically require a user to place a finger in a cavity or bowl to pinch or otherwise manipulate the contact lens so it can be removed. The contact lens then needs to be positioned on a fingertip so it can be placed on an eye. Handling the contact lens, however, can introduce contaminants to the surface of the lens which can then be transferred to the eye. It can be appreciated that there remains a need to improve contact lens packaging, which, among other things, presents a contact lens in a position whereby it can be directly placed on a fingertip in a position enabling placement directly onto an eye. There also remains a need to provide a multi-lens dispenser that enables push-button application of a contact lens onto a fingertip.

SUMMARY OF THE INVENTION

The present contact lens dispenser, when actuated, presents the contact lens in an orientation that enables direct placement of the lens onto a fingertip for easy transfer of the lens to the surface of an eye. No digging into a cavity or bowl or pinching of an unworn lens is required to place the lens in a desired orientation for placement onto an eye. Moreover, the present contact lens package, when opened, presents the lens in an orientation that does not require touching the inner, concave surface of the lens that, in use, directly contacts the surface of an eye.

According to the present invention, a contact lens dispenser is provided. In a first embodiment, the dispenser comprises a tubular housing having an interior and a dispensing end. A delivery screw is provided in the interior of the tubular housing. The delivery screw has a thread and an axis of rotation. The thread has a pitch, and the delivery screw is mounted for rotation within the tubular housing about the axis of rotation. An actuator is provided that is configured to rotate the dispensing screw upon actuation. A plurality of contact lenses are disposed in the interior of the tubular housing. The contact lenses are suspended in a contact lens solution, while the lenses are located on the thread. The contact lenses are spaced apart from one another, along the thread, by the pitch. The thread is configured to hold the contact lenses and the contact lens solution along the thread. Upon actuation of the actuator, each of the contact lenses is moved along the thread by a distance of one pitch and a single contact lens is dispensed from the dispensing end of the tubular housing.

A method of dispensing a contact lens from a dispenser is also provided by the present invention. The dispenser can be of a dispenser pen type as described herein.

In another embodiment of the present invention, a contact lens dispenser is provided that comprises a case and a disposable foil contact lens cartridge. The case comprises an actuator, a slot, and a dispensing outlet. The slot is configured to receive the disposable foil contact lens cartridge. The disposable foil contact lens cartridge comprises a plurality of contact lenses and a plurality of blisters. Each of the contact lenses is blister-sealed individually in a respective one of the blisters. The disposable foil contact lens cartridge has a size and shape enabling (i) insertion of the cartridge into the slot and (ii) alignment of the blisters, one at a time, with the actuator and the dispensing outlet. Upon insertion of the disposable foil contact lens cartridge in the slot and actuation of the actuator, the actuator pierces a blister aligned with both the actuator and the dispensing outlet. The piercing forms a pierced blister and the actuation further forces the contact lens from within the pierced blister to be delivered to the dispensing outlet of the case. The disposable foil contact lens cartridge can have a flat, circular shape and a central axis of rotation. The actuator can be configured to spin the disposable foil contact lens cartridge about the central axis of rotation to advance the blisters of the plurality of blisters such that a new unpierced blister is moved into alignment with the actuator. The spinning or other movement of the disposable foil contact lens cartridge can be caused during, or upon completion of, a piercing and dispensing operation.

According to yet another embodiment of the present invention, a contact lens dispenser is provided comprising a case and a disposable contact lens foil spool. The case comprises an actuator, a reel configured to receive the contact lens foil spool, and a dispensing outlet. The disposable contact lens foil spool can comprise a plurality of contact lenses and a plurality of blisters. Each of the contact lenses can be blister-sealed individually in a respective one of the blisters. The disposable contact lens foil spool can have a size and shape enabling (i) insertion of the spool onto the reel of the case, and (ii) alignment of the blisters, one at a time, with the actuator and the dispensing outlet.

Other aspects and details of the present invention will be apparent based on the following drawings, detailed description, and claims.

BRIEF DESCRIPTION OF THE DRAWINGS

FIG. 3A is a side view of a dispenser pen in accordance with an embodiment of the present invention.

FIG. 3B is a front, right perspective view of the dispenser pen shown in FIG. 3A.

FIG. 3C is a cross-sectional side view of the dispenser pen shown in FIGS. 3A and 3B.

FIG. 3D is a cross-sectional side view of the dispenser pen shown in FIGS. 3A-3C but loaded with a plurality of contact lenses and dispensing a single contact lens.

FIG. 4 is a top, right perspective view of a disposable foil contact lens blister cartridge according to an embodiment of the present invention.

FIG. 5 is a perspective of a dispenser case receiving a blister cartridge as shown in FIG. 4, in accordance with an embodiment of the present invention.

FIG. 6 illustrates a dispensing method whereby the of the case shown in FIG. 5 has been actuated and a contact lens is dispensed out of the dispensing outlet of the case onto a fingertip of a user and in a position for immediate application onto an eye.

DETAILED DESCRIPTION

Figure 2:
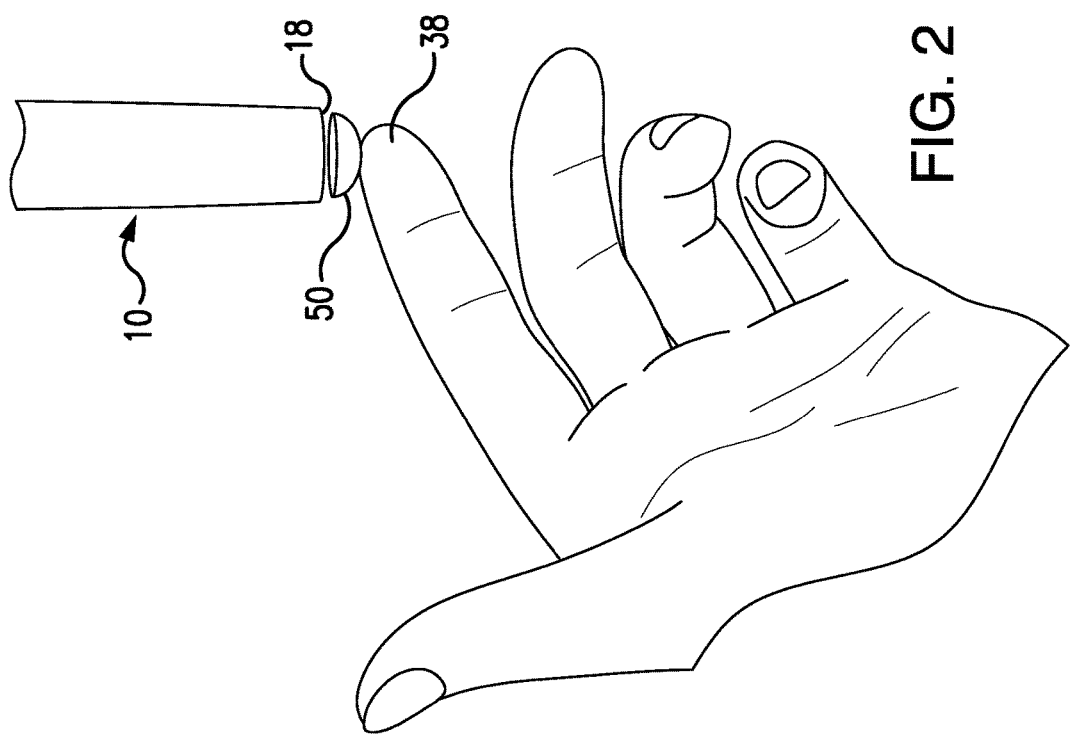
FIG. 2 illustrates how a contact lens can be dispensed from a dispensing end of the dispenser shown in FIG. 1, directly onto a fingertip.

A contact lens dispenser is provided in accordance with the present invention. In a first embodiment, the dispenser comprises a tubular housing having an interior and a dispensing end. A delivery screw is provided in the interior of the tubular housing. The delivery screw has a thread and an axis of rotation. The thread has a pitch, and the delivery screw is mounted for rotation within the tubular housing about the axis of rotation. An actuator is provided that is configured to rotate the dispensing screw upon actuation. A plurality of contact lenses is disposed in the interior of the tubular housing. The contact lenses are suspended in a contact lens solution, on the thread. The contact lenses are spaced apart from one another, along the thread, by the pitch. The thread is configured to hold the contact lenses and the contact lens solution along the thread. In some embodiments, the thread and contact lenses are immersed in the contact lens solution. Upon actuation of the actuator, each of the contact lenses is moved along the thread by a distance of one pitch and a single contact lens is dispensed from the dispensing end of the tubular housing.

The contact lens dispenser can be in the shape of a pen. The actuator can be disposed at an actuating end of the tubular housing, opposite the dispensing end. The contact lens dispenser can further comprise a seal at the dispensing end of the tubular body. The seal can be configured to prevent the dispensing of more than one contact lens at-a-time from the dispensing end, upon actuation of the actuator. In other words, only a single contact lens is dispensed per actuation of the actuator. The screw can comprise a seal actuator that lifts the seal upon actuation of the actuator, enabling a single contact lens along the thread to pass to the dispensing end of the tubular housing. The actuator can comprise a ratcheting button actuator. The actuator can comprise a rotatable knob, for example, a ratcheting rotatable knob.

The thread of the dispensing screw has an outer diameter. The tubular housing has an inner diameter. The outer diameter of the dispensing screw can be about the same as the inner diameter of the tubular housing. Each pitch of the dispensing thread can comprise a frangible seal that seals a contact lens and lens solution in a sealed pouch until the contact lens is dispensed from the dispenser. The thread of the dispensing screw can have an outer edge that fits snuggly but movably against the inner sidewall of the tubular housing. The outer edge can comprise of hydrophobic material.

A method of dispensing a contact lens from a dispenser is also provided by the present invention. The dispenser can be of a type as described herein, particularly having a tubular housing and a delivery screw in an interior of the tubular housing. The delivery screw has a thread and an axis of rotation. The thread has a pitch, and the delivery screw is mounted for rotation within the tubular housing about the axis of rotation. An actuator is provided to rotate the dispensing screw upon actuation. A plurality of contact lenses are disposed in the interior of the tubular housing and the contact lenses are suspended in separate aliquots of contact lens solution, for example, in frangible pouches spaced apart on the thread. The contact lenses can be spaced apart from one another, along the thread, by the pitch. The method can comprise actuating the actuator such that each of the contact lenses is moved along the thread by a distance of one pitch and a single contact lens is dispensed from the dispensing end of the tubular housing. The method can involve catching the dispensed lens as it leaves the tubular housing. The catching can comprise catching the dispensed contact lens on a tip of a finger, for example, as the contact lens exits the tubular housing. The dispensed contact lens can be caught in the palm of a hand, although dispensing directly onto a user's fingertip can be useful in minimizing contamination.

In yet another embodiment of the present invention, a contact lens dispenser is provided that comprises a case and a disposable foil contact lens cartridge. The case comprises an actuator, a slot, and a dispensing outlet. The slot is configured to receive the disposable foil contact lens cartridge. The disposable foil contact lens cartridge comprises a plurality of contact lenses and a plurality of blisters. Each of the contact lenses is blister-sealed individually in a respective one of the blisters. The disposable foil contact lens cartridge has a size and shape enabling (i) insertion of the cartridge into the slot and (ii) alignment of the blisters, one at a time, with the actuator and the dispensing outlet. Upon insertion of the disposable foil contact lens cartridge in the slot and actuation of the actuator, the actuator pierces a blister aligned with both the actuator and the dispensing outlet. The piercing forms a pierced blister and the actuation further forces the contact lens from within the pierced blister to be delivered to the dispensing outlet of the case.

The contact lens dispenser can use a disposable foil contact lens cartridge that has a flat, circular shape and a central axis of rotation. The actuator can be configured to spin the disposable foil contact lens cartridge about the central axis of rotation to advance the blisters of the plurality of blisters such that a new unpierced blister is moved into alignment with the actuator. The spinning or other movement of the disposable foil contact lens cartridge can be caused during, or upon completion of, a piercing and dispensing operation. A ratchet can be implemented to effect movement of the disposable foil contact lens cartridge. A central hole can be provided in the disposable foil contact lens cartridge so that it can spin about a pin or other axle that is part of the case. The case can also comprise a counter to track the number of unpierced blisters remaining in the disposable foil contact lens cartridge. The actuator can be configured to deliver a contact lens from a pierced blister through the dispensing outlet, in a convex-first orientation. As such, the contact lens can be presented to a user's fingertip in the correct orientation, convex-side-first, so that once it is caught by or dispensed onto a fingertip the contact lens is in the correct orientation to be immediately applied to an eye.

According to yet another embodiment of the present invention, a contact lens dispenser is provided that comprises a case and a disposable contact lens foil spool. The case comprises an actuator, a reel configured to receive the contact lens foil spool, and a dispensing outlet. The disposable contact lens foil spool can comprise a plurality of contact lenses and a plurality of blisters. Each of the contact lenses can be blister-sealed individually in a respective one of the blisters. The disposable contact lens foil spool can have a size and shape enabling (i) insertion of the spool onto the reel of the case, and (ii) alignment of the blisters, one at a time, with the actuator and the dispensing outlet.

Upon mounting the spool onto the reel and actuation of the actuator, the actuator pierces a blister aligned with both the actuator and the dispensing outlet. The piercing forms a pierced blister. The actuation further forces the contact lens from within the pierced blister to be delivered to the dispensing outlet of the case. The actuator can be configured to turn the disposable contact lens foil spool about a central axis thereof to advance the next, unpierced blister of the plurality of blisters into alignment with the actuator during, or upon completion of, a piercing and dispensing operation. The case can comprise a counter to track the number of unpierced blisters remaining in the disposable contact lens foil spool, or the number of pierced blisters. The actuator can be configured to deliver a contact lens from a pierced blister through the dispensing outlet, in a convex-first orientation. As such, the contact lens can be presented to a user's fingertip in the correct orientation for immediate application to an eye.

The blisters described herein include a well or volume for containing a contact lens immersed in an amount of a solution. The term "contact lens" as used herein is intended to embrace an ophthalmic lens which, after its removal from a mold assembly in which it is made, is of a structure, size, shape and power that it can be worn on or in the eye of an individual. The blister is designed to cover and sealingly enclose the contact lens and solution within the volume.

The body of the blister foil cartridge or reel can be formed of a plastic material that can be shaped by injection molding or thermoforming. The plastic material used to make the blister can comprise polypropylene, polyethylene, polystyrene, or another thermoplastic material. One or more portions of the blister can have a vapor transmission of less than 10 grams/100 square inches/24 hours at 70° F. and 50 percent relative humidity.

The blister cartridge or reel can comprise a variety of structures, such as a relatively rigid material or a flexible material. The sealed blisters can be made of a thermoplastic material. Each blister can comprise a well and a substantially planar body top surface surrounding the well. The substantially planar body top surface provides a sealing surface for sealing a seal to the top of the blister well. The blister can be made from a variety of materials. The blister cartridge or reel can be formed using conventional methods and equipment, such as by injection molding polypropylene resin into body molds in an injection molding machine. Each entire blister, blister top, or blister bottom can be formed from a variety of materials. For example, the blister can be a laminated structure comprising a foil and one or more layers of plastic, such as polypropylene and the like. The blister can include human readable information, as desired. The blister can include a top coupled to a body by contacting the sealing surface of the body with the top and applying heat to fuse the two members together to provide a hermetic or airtight seal for the contact lens and the packaging solution in the blister.

The perimeter of the blister well or volume can be contiguous with a circumference of the well or volume. The blister can include a well, the perimeter of the well can include a flange region, and the flange region can extend, for example, about 5 mm from the opening of the well to a grip region. In an exemplary embodiment, the blister cartridge can comprise a circular disk shape about three to five inches in diameter. It should be appreciated, however, that the blister cartridge or blister reel can have any size and/or shape.

The blister holds in a fluid tight manner, a contact lens and solution. A top of the blister can be attached to a body of the blister by heat-sealing in a seal area; however, induction-sealing, sonic welding, or other bonding systems can be used to attach the blister top to the blister body. The total interior volume defined by the blister, once sealed, can be about 2.2 ml or less. The volume of the packaging solution in the bowl can be, for example, from about 0.5 ml to about 2.5 ml.

One or more layers of the blister can comprise at least two elements, for example, at least two different, separate layers of material. For example, a blister top can comprise a first member, or first layer, and a second member, or second layer overlaying the first member. The first member can be made of a laminate material that is heat sealed to a seal region of a blister body. The second member can comprise a foil material, sealed to a rim portion of a blister body. The second member can comprise at least one, for example two, polymer layers, e.g. polypropylene, coating a foil. The foil can comprise a metal foil, such as aluminum foil. The polymer coating material on a heat seal side of the foil can be polypropylene. Examples of useful cover layers are described in U.S. Pat. No. 4,691,820 that is incorporated herein in its entirety by reference. The second member can be sealed to a blister body along an entire circumference of the body surrounding the well, so as to provide a sanitary or sterile covering, for example, by means of a hermetic seal.

An unworn contact lens is sealed within the blister and is packaged in a contact lens packaging solution. Any contact lens can be packaged therein. For example, the contact lens can be a hydrogel contact lens, or it can be a silicone hydrogel contact lens. Examples of contact lenses that can be provided in the packages include those having the following United States Adopted Names (USANs): methafilcon A, ocufilcon A, ocufilcon B, ocufilcon C, ocufilcon D, omafilcon A, omafilcon B, comfilcon A, enfilcon A, stenfilcon A, etafilcon A, senofilcon A, senofilcon B, senofilcon C, narafilcon A, narafilcon B, balafilcon A, samfilcon A, lotrafilcon A, lotrafilcon B, somofilcon A, riofilcon A, delefilcon A, and the like.

The fluid medium or solution (i.e., the packaging solution) contained in the blister can be any known solution useful for storing contact lenses, including water, saline solutions, or buffered aqueous solutions. The contact lens and solution will preferably fill at least 50 percent, for example, at least 70 percent or at least 80 percent, of the total volume defined by the blister once sealed.

The contact lens packaging solution is typically a buffered saline solution, such as a phosphate buffered saline solution, or a borate buffered saline solution, that can contain one or more additives, such as surfactants, wetting agents, viscosity agents, and the like.

The blister package can also include a wrap that has one or more panels. The wrap can be dimensioned to accommodate the sealed contact lens package and to also provide an UDI in both human readable form and machine-readable form, in addition to other required regulatory information. As used herein, a UDI is a "Unique Device Identifier". As used herein, a wrap refers to a substrate or article comprising one or more panels coupled to a sealed contact lens blister cartridge or reel, and an UDI in both human readable form and machine-readable form is provided on at least one of the panels. Such a wrap can be understood to be an "UDI wrap", or it can be understood to be a wrap having an "UDI panel". Thus, the wrap includes human readable information, such as letters, numbers, and images; and the wrap includes machine readable information, such as bar codes and the like. The wrap can be flexible or rigid and does not need to fully enclose or surround the individual sealed contact lens blisters. The wrap can be coupled to the sealed contact lens package so that the wrap and sealed contact lens package do not become separated until a person opens the package to remove the blister cartridge or reel before installation into a case. For example, the wrap can be adhered to a sealed contact lens blister foil cartridge or a contact lens reel, for example, by using an adhesive between a surface of the wrap and a surface of the cartridge or reel. The wrap can be physically wrapped around the cartridge or reel to mechanically enclose the cartridge or reel within the wrap. Thus, the wrap cannot be inadvertently dislodged or separated from the sealed cartridge or reel.

Examples of blister package materials, methods of making blister package bodies, flexible tops, methods of making flexible tops, methods of sealing flexible tops to bodies, as well as other helpful components, materials, methods, and systems are described, for example, in U.S. Pat. Nos. 6,398,018, 7,426,993 B2, and 7,477,366 B2, in U.S. Patent Application Publications Nos. US 2012/0061260 A1, and US 2017/0096272 A1, and in WO 2013/160667, each of which is incorporated herein in its entirety by reference.

Figure 1:
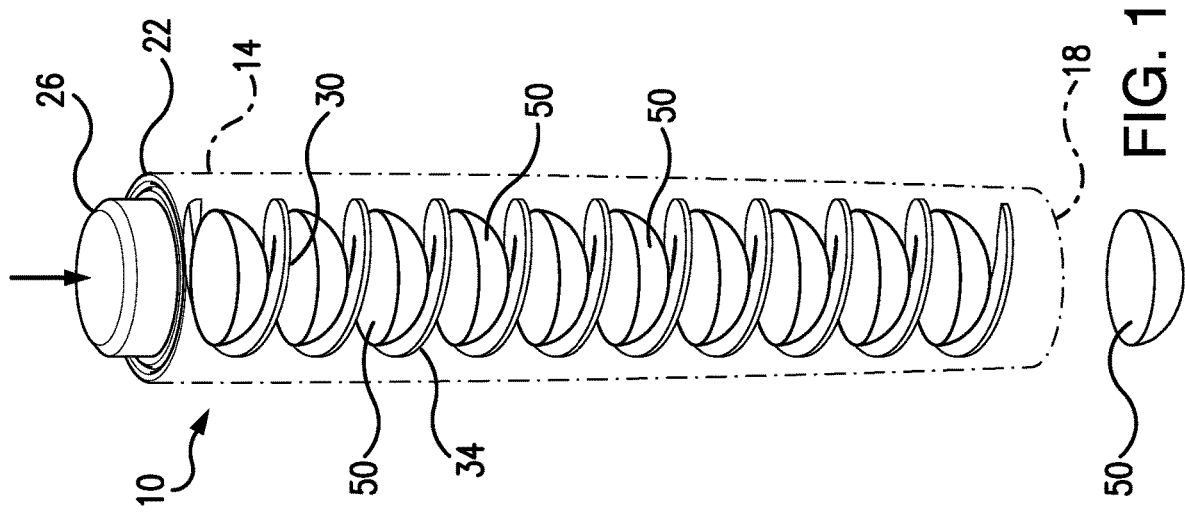
FIG. 1 is a side view of a contact lens dispenser pen 10, in partial see-through, in accordance with an embodiment of the present invention.

FIG. 1 is a side view of a contact lens dispenser pen 10, in partial see-through, in accordance with an embodiment of the present invention. Pen 10 comprises a tubular housing 14 having a dispensing end 18 and an actuator end 22. An actuator 26 can be depressed, for example, by a finger, toward tubular housing 14, to cause rotation of an Archimedes screw 30. Archimedes screw 30 can rotate around an axis of rotation within an interior 34 of tubular housing 14. In an example, each depression of actuator 26 can cause one full rotation of Archimedes screw 30, whereby, with each depression of actuator 26 and corresponding rotation of Archimedes screw 30, a contact lens 50 is dispensed out of dispensing end 18. As can be seen in FIG. 2, a contact lens 50 can be dispensed from dispensing end 18 directly onto a fingertip, for example, of a user.

FIGS. 3A-3D are various views of a pen 300 in accordance with an embodiment of the present invention. FIG. 3A is a side view of a pen 300. Pen 300 includes a tubular housing 314, a dispensing end 318, an actuator end 322, and an actuator 326. Inside tubular housing 314 is an Archimedes screw 330, as shown in FIGS. 3B-3D. FIG. 3B is a front, right perspective view of pen 300. Archimedes screw 330 can be seen through the open dispensing end 318. FIG. 3C is a cross-sectional side view of pen 300. FIG. 3D is a cross-sectional side view of the dispenser pen shown in FIGS. 3A-3C but loaded with a plurality of contact lenses 350 suspended in contact lens solution 352 and dispensing a single contact lens 351. FIG. 3D further illustrates an outer edge 331 of the Archimedes screw 330 in contact with an inner sidewall 315 of the tubular housing 314. Any well-known ratcheting arrangement can be used to provide an actuatable ratcheting rotation of Archimedes screw 330.

Archimedes screw 330 has threads 332, separated from one another by one full 360° rotation of Archimedes screw 330. Threads 332 are separated from adjacent threads by a pitch 336. One contact lens 350 is provided per pitch 336. The actuator can be geared such that one contact lens 350 is dispensed per actuation of actuator 326.

FIG. 4 is a top perspective view of a disposable foil contact lens blister cartridge 400 according to another embodiment of the present invention. A foil top seal 410 seals a plurality of blisters 420 between an inner surface of top seal 410 and an upper surface of an underlying body. Blister cartridge 400 can be inserted into a slot 510 of a case 500 as shown in FIG. 5. An actuator 520 in the form of a push-button is provided in the center of a sidewall 530 of case 500. Upon closing case 500 with blister cartridge 400 loaded therein, and pushing to actuate push-button 520, a contact lens 550 is dispensed from a dispensing outlet 540. FIG. 6 illustrates a dispensing method whereby actuator 520 has been actuated and a contact lens 550 is dispensed out of dispensing outlet 540 onto a fingertip 538 of a user and in a position for immediate application onto an eye.

Figure 8:
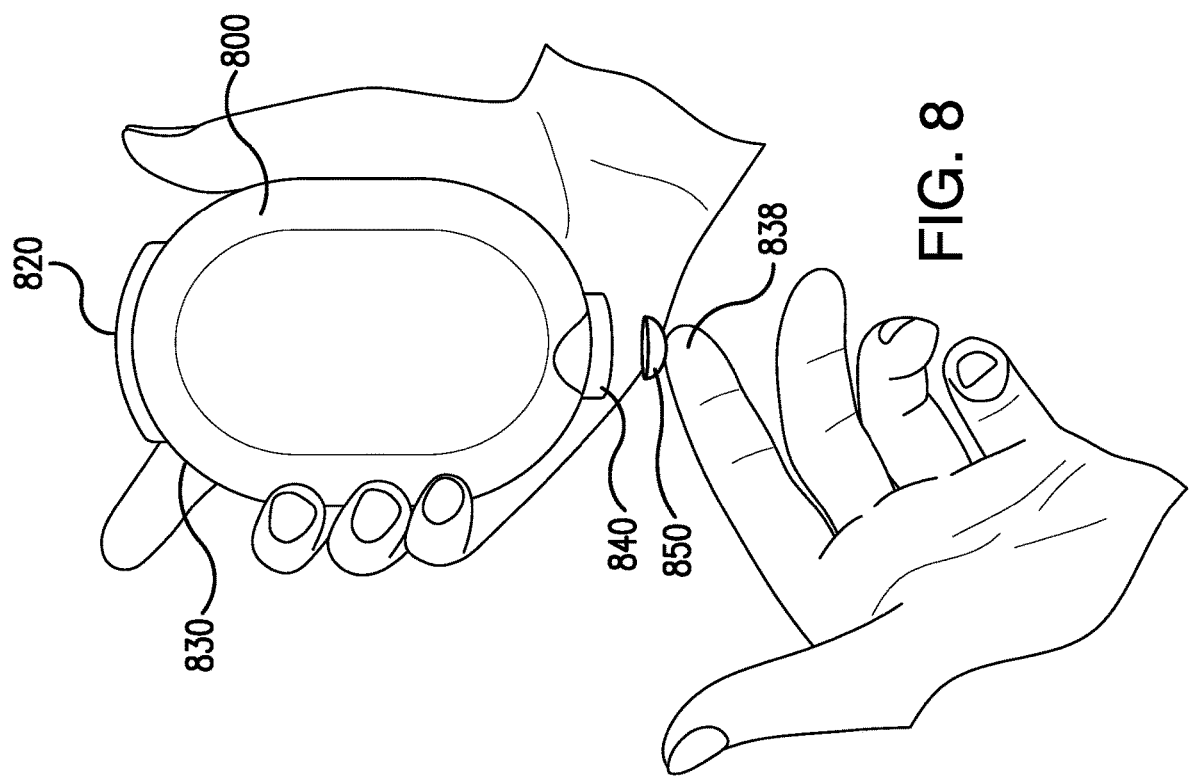
FIG. 8 illustrates a dispensing method whereby an actuator of a reel dispensing case has been actuated and a contact lens is dispensed out of a dispensing outlet of the case and onto a fingertip of a user, in a position for immediate application onto an eye.
Figure 7:
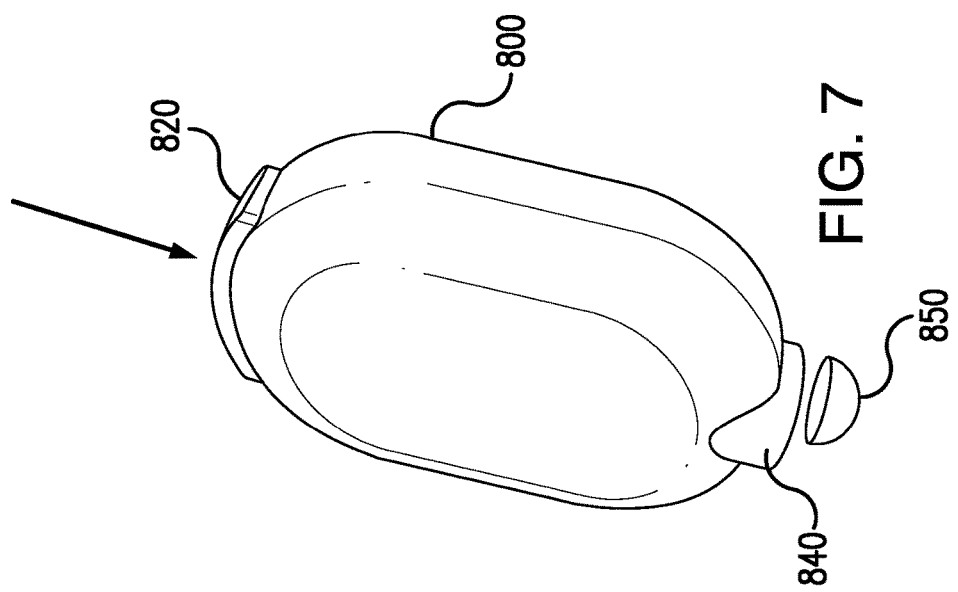
FIG. 7 is a front, right, top perspective view of a blister reel dispensing case for dispensing contact lenses from a reel of blister-packaged contact lenses, in accordance with an embodiment of the present invention.

FIG. 7 is a front, right, top perspective view of a blister reel dispensing case 800 for dispensing contact lenses from a reel of blister-packaged contact lenses. An actuator 820 in the form of a push-button is provided at the top 830 of case 800. Upon installing a reel of blister packages on a spool within case 800, and closing case 800 with a blister reel loaded therein, and pushing to actuate push-button 820, a contact lens 850 is dispensed from a dispensing outlet 840. FIG. 8 illustrates a dispensing method whereby actuator 820 has been actuated and a contact lens 850 is dispensed out of dispensing outlet 840 onto a fingertip 838 of a user and in a position for immediate application onto an eye.

The present invention includes the following aspects/embodiments/features in any order and/or in any combination:

1. A contact lens dispenser comprising:
   a tubular housing having an interior and a dispensing end;
   a delivery screw in the interior of the tubular housing, the delivery screw comprising a thread and having an axis of rotation, the thread having a pitch, and the delivery screw mounted for rotation within the tubular housing about the axis of rotation; and
   an actuator configured to rotate the dispensing screw upon actuation of the actuator wherein a plurality of contact lenses is disposed in the interior, suspended in solution, on the thread, the contact lenses are each spaced apart from adjacent ones, along the thread, by the pitch, and the thread is configured to hold the contact lenses and the contact lens solution along the thread such that, upon actuation of the actuator, each of the contact lenses is moved along the thread by a distance of one pitch and a single contact lens is dispensed from the dispensing end of the tubular housing.

2. The contact lens dispenser of any preceding or following embodiment/feature/aspect, wherein the actuator is disposed at an actuating end of the tubular housing, opposite the dispensing end.

3. The contact lens dispenser of any preceding or following embodiment/feature/aspect, further comprising a seal at the dispensing end of the tubular body, a seal being configured to prevent the dispensing of more than one contact lens from the dispensing end upon actuation of the actuator.

4. The contact lens dispenser of any preceding or following embodiment/feature/aspect, wherein the screw comprises a seal actuator that lifts the seal upon actuation of the actuator, enabling a single contact lens along the thread to pass to the dispensing end of the tubular housing.

5. The contact lens dispenser of any preceding or following embodiment/feature/aspect, wherein the actuator comprises a ratcheting button actuator.

6. The contact lens dispenser of any preceding or following embodiment/feature/aspect, wherein the actuator comprises a rotatable knob.

7. The contact lens dispenser of any preceding or following embodiment/feature/aspect, wherein the thread of the dispensing screw has an outer diameter, the tubular housing has an inner diameter, and the outer diameter and the inner diameter are the same.

8. The contact lens dispenser of any preceding or following embodiment/feature/aspect, wherein the thread of the dispensing screw has an outer edge, the tubular housing has an inner sidewall, and the outer edge of the thread fits snuggly against the inner sidewall.

9. The contact lens dispenser of any preceding or following embodiment/feature/aspect, wherein the outer edge comprises of hydrophobic material.

10. A method of dispensing a contact lens from a contact lens dispenser, the contact lens dispenser comprising
a tubular housing having an interior and a dispensing end,
a delivery screw in the interior of the tubular housing, the delivery screw comprising a thread and having an axis of rotation, the thread having a pitch, and the delivery screw mounted for rotation within the tubular housing about the axis of rotation,
an actuator configured to rotate the dispensing screw upon actuation of the actuator, and
a plurality of contact lenses is disposed in the interior, suspended in solution, on the thread, the contact lenses being each spaced apart from adjacent ones, along the thread, by the pitch, and the thread being configured to hold the contact lenses and the contact lens solution along the thread, wherein the method comprises:
actuating the actuator to move each of the contact lenses along the thread by a distance of one pitch and cause a single contact lens to be dispensed from the dispensing end of the tubular housing.

11. The method of any preceding or following embodiment/feature/aspect, further comprising catching the contact lens as it is dispensed from the dispensing end of the tubular housing, on an applicator.

12. The method of any preceding or following embodiment/feature/aspect, wherein the catching the contact lens as it is dispensed from the dispensing end of the tubular housing comprises catching the contact lens on a fingertip.

13. A contact lens dispenser comprising:
a case comprising an actuator, a slot, and a dispensing outlet, the slot configured to receive a disposable foil contact lens cartridge; and
a disposable foil contact lens cartridge comprising a plurality of contact lenses and a plurality of blisters, each of the contact lenses being blister-sealed individually in a respective one of the blisters, the disposable foil contact lens cartridge having a size and shape enabling (i) insertion into the slot and (ii) alignment of the blisters, one at a time, with the actuator and the dispensing outlet, wherein
upon insertion of the disposable foil contact lens cartridge in the slot and actuation of the actuator, the actuator pierces a blister aligned with both the actuator and the dispensing outlet, forming a pierced blister, and forces the contact lens from within the pierced blister to be delivered to the dispensing outlet of the case.

14. The contact lens dispenser of any preceding or following embodiment/feature/aspect, wherein the disposable foil contact lens cartridge has a flat, circular shape and a central axis of rotation.

15. The contact lens dispenser of any preceding or following embodiment/feature/aspect, wherein the actuator is configured to spin the disposable foil contact lens cartridge about the central axis of rotation to advance the blisters of the plurality of blisters into alignment with the actuator during, or upon completion of, a piercing and dispensing operation.

16. The contact lens dispenser any preceding or following embodiment/feature/aspect, wherein the case comprises a counter to track the number of unpierced blisters remaining in the disposable foil contact lens cartridge.

17. The contact lens dispenser of any preceding or following embodiment/feature/aspect, wherein the actuator is configured to deliver a contact lens from a pierced blister through the dispensing outlet, in a convex-first orientation such that the lens can be presented to a user's fingertip in the correct orientation for immediate application to an eye.

18. A contact lens dispenser comprising:
a case comprising an actuator, a reel configured to receive a contact lens foil spool cartridge, and a dispensing outlet; and
a disposable contact lens foil spool comprising a plurality of contact lenses and a plurality of blisters, each of the contact lenses being blister-sealed individually in a respective one of the blisters, the disposable contact lens foil spool having a size and shape enabling (i) insertion onto the reel of the case, and (ii) alignment of the blisters, one at a time, with the actuator and the dispensing outlet, wherein
upon mounting the spool onto the reel and actuation of the actuator, the actuator pierces a blister aligned with both the actuator and the dispensing outlet, forming a pierced blister, and forces the contact lens from within the pierced blister to be delivered to the dispensing outlet of the case.

19. The contact lens dispenser of any preceding or following embodiment/feature/aspect, wherein the actuator is configured to turn the disposable contact lens foil spool about a central axis thereof to advance a blister of the plurality of blisters into alignment with the actuator during, or upon completion of, a piercing and dispensing operation.

20. The contact lens dispenser of any preceding or following embodiment/feature/aspect, wherein the case comprises a counter to track the number of unpierced blisters remaining in the disposable contact lens foil spool.

21. The contact lens dispenser of any preceding or following embodiment/feature/aspect, wherein the actuator is configured to deliver a contact lens from a pierced blister through the dispensing outlet, in a convex-first orientation such that the lens can be presented to a user's fingertip in the correct orientation for immediate application to an eye.

The present invention can include any combination of these various features or embodiments above and/or below as set-forth in sentences and/or paragraphs. Any combination of disclosed features herein is considered part of the present invention and no limitation is intended with respect to combinable features.

The entire contents of all references cited in this disclosure are incorporated herein in their entireties, by reference. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether such ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A contact lens dispenser comprising:
    a tubular housing having an inner sidewall, an interior defined by the inner sidewall, and a dispensing end;
    a delivery screw in the interior of the tubular housing and surrounded by the inner sidewall, the delivery screw comprising a thread having an outer edge and the delivery screw having an axis of rotation, the thread having a pitch, and the delivery screw mounted for rotation within the tubular housing about the axis of rotation, wherein the outer edge is in contact with the inner sidewall; and
    an actuator configured to rotate the dispensing screw upon actuation of the actuator wherein
    a plurality of contact lenses is disposed in the interior, suspended in solution, on the thread, the contact lenses are each spaced apart from adjacent ones, along the thread, by the pitch, and the thread is configured to hold the contact lenses and the contact lens solution along the thread such that, upon actuation of the actuator, each of the contact lenses is moved along the thread by a distance of one pitch and a single contact lens is dispensed from the dispensing end of the tubular housing.

2. The contact lens dispenser of claim 1, wherein the actuator is disposed at an actuating end of the tubular housing, opposite the dispensing end.

3. The contact lens dispenser of claim 1, further comprising a seal at the dispensing end of the tubular body.

4. The contact lens dispenser of claim 1, wherein the actuator comprises a rotatable knob.

5. The contact lens dispenser of claim 1, wherein the thread of the dispensing screw has an outer diameter, the tubular housing has an inner diameter, and the outer diameter and the inner diameter are about the same.

6. The contact lens dispenser of claim 1, wherein the outer edge comprises of hydrophobic material.

7. A method of dispensing a contact lens, comprising:
    actuating the actuator of the contact lens dispenser of claim 1 to present a contact lens at the dispensing end of the tubular housing; and
    touching the contact lens presented to a tip of a finger of a user.

* * * * *